(12) United States Patent
Collins et al.

(10) Patent No.: US 11,980,729 B2
(45) Date of Patent: May 14, 2024

(54) ACTUATING MECHANISM FOR FLUID DISPLACEMENT AND PRESSURIZING DEVICES

(71) Applicant: Atrion Medical Products, Inc., Arab, AL (US)

(72) Inventors: Jonathan Collins, Arab, AL (US); Rowland Kanner, Guntersville, AL (US); Brian Roberts, Owens Cross Roads, AL (US)

(73) Assignee: Atrion Medical Products, Inc., Arab, AL (US)

( * ) Notice: Subject to any disclaimer, the term of this patent is extended or adjusted under 35 U.S.C. 154(b) by 134 days.

(21) Appl. No.: 17/488,744

(22) Filed: Sep. 29, 2021

(65) Prior Publication Data
US 2022/0193380 A1 Jun. 23, 2022

Related U.S. Application Data

(60) Provisional application No. 63/127,369, filed on Dec. 18, 2020.

(51) Int. Cl.
*A61M 25/10* (2013.01)

(52) U.S. Cl.
CPC .............................. *A61M 25/10182* (2013.11)

(58) Field of Classification Search
CPC ........ A61M 25/10182; A61M 25/1018; A61M 5/315; A61M 5/31513; A61M 5/31511; A61M 5/48; A61M 5/5066; A61M 2005/31508
See application file for complete search history.

(56) References Cited

U.S. PATENT DOCUMENTS

| 4,838,864 A | 6/1989 | Peterson |
| 4,919,121 A | 4/1990 | Rydell et al. |
| 5,047,015 A | 9/1991 | Foote et al. |
| 5,057,078 A | 10/1991 | Foote et al. |
| 5,168,757 A | 12/1992 | Rabenau et al. |
| 5,209,732 A | 5/1993 | Lampropoulos et al. |
| 6,796,959 B2 | 9/2004 | Davis et al. |
| 7,530,970 B2 | 5/2009 | McArthur et al. |
| 9,492,643 B2 | 11/2016 | Kanner et al. |
| 10,842,973 B2 | 11/2020 | Lampropoulos et al. |
| 11,202,890 B2 | 12/2021 | Kanner et al. |

(Continued)

FOREIGN PATENT DOCUMENTS

| CN | 106438329 B | 6/2017 | |
| FR | 2676928 A1 * | 12/1992 | .......... A61M 5/5066 |

(Continued)

*Primary Examiner* — Laura A Bouchelle
*Assistant Examiner* — Sarah Dympna Grasmeder
(74) *Attorney, Agent, or Firm* — Clark Hill PLC; James R. Foley

(57) ABSTRACT

A fluid displacement and pressurization device which provides both a substantial amount of thread engagement as well as provides for single hand control for all operational manipulations including maintaining a set fill volume, rapid filling and displacement, and pressurization and retention of evacuation positioning during balloon depressurization. The device allows for the use of one hand to not only transition the device from micro-movement control to macro-movement control, but also regarding rotating, pushing or pulling the handle of the plunger.

25 Claims, 9 Drawing Sheets

(56) References Cited

U.S. PATENT DOCUMENTS

| | | | |
|---|---|---|---|
| 2003/0120219 A1* | 6/2003 | Nielsen | A61M 5/31511 604/228 |
| 2006/0129107 A1* | 6/2006 | McArthur | A61M 25/10182 604/208 |
| 2010/0130935 A1* | 5/2010 | Hieb | A61M 5/007 604/220 |
| 2014/0088498 A1 | 3/2014 | Stevens et al. | |
| 2016/0279395 A1* | 9/2016 | Lampropoulos | A61M 25/10181 |
| 2017/0246433 A1 | 8/2017 | Kanner et al. | |
| 2020/0229855 A1 | 7/2020 | Purdy et al. | |

FOREIGN PATENT DOCUMENTS

| | | | | |
|---|---|---|---|---|
| WO | 90/11101 A1 | 10/1990 | | |
| WO | 92/07609 A1 | 5/1992 | | |
| WO | 2019/199901 A1 | 10/2019 | | |
| WO | WO-2019199901 A1 * | 10/2019 | | A61F 9/0008 |

* cited by examiner

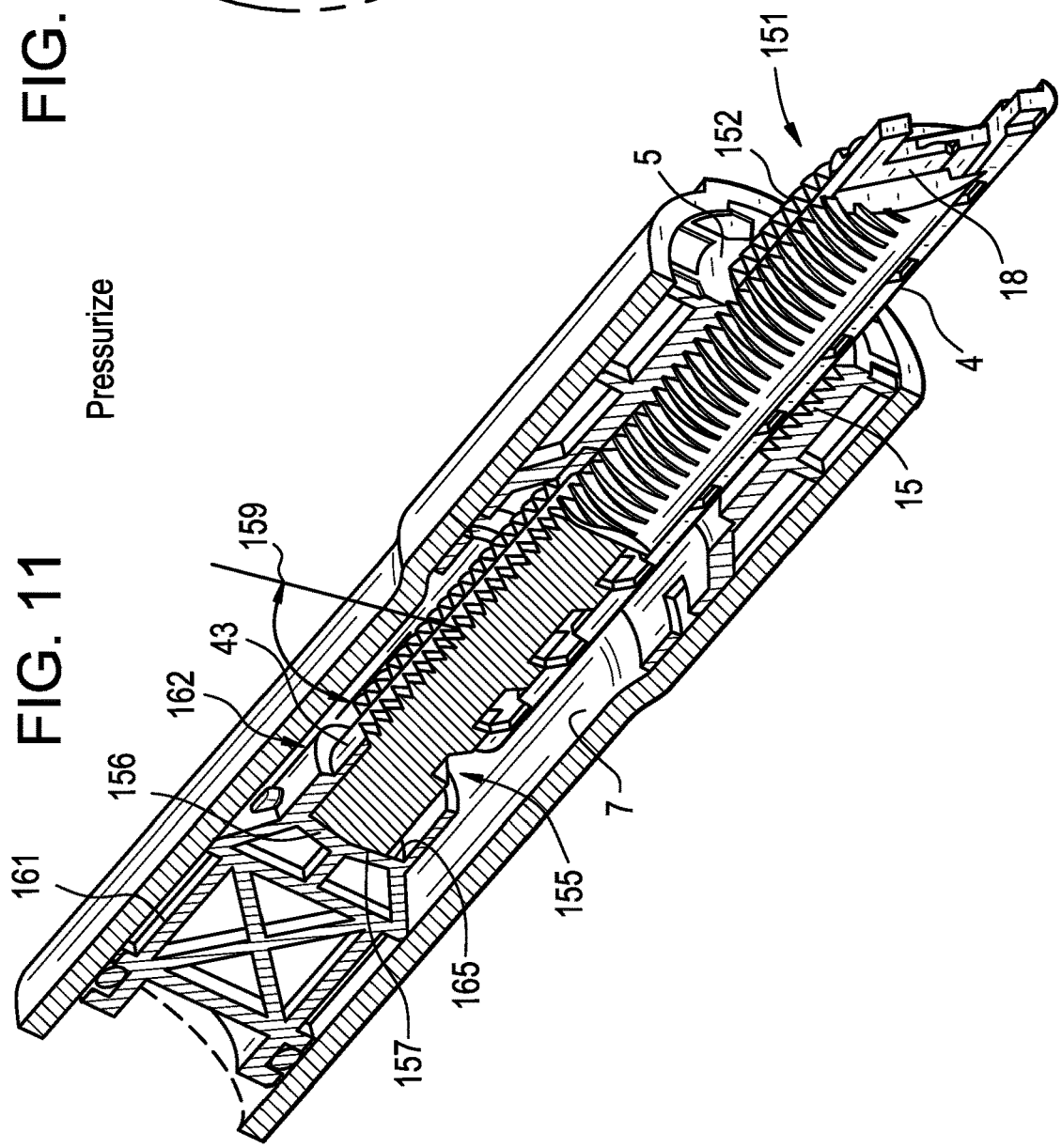

ACTUATING MECHANISM FOR FLUID DISPLACEMENT AND PRESSURIZING DEVICES

RELATED APPLICATION (PRIORITY CLAIM)

This application claims the benefit of U.S. Provisional Application Ser. No. 63/127,369, filed Dec. 18, 2020, which is hereby incorporated herein by reference in its entirety.

BACKGROUND

The present invention generally relates to fluid displacement and pressurizing devices for balloon catheters or the like, and more particularly relates to an improved screw plunger actuation and drive mechanism to control the displacement and pressurization of the working fluid.

Fluid displacement and pressurization devices adapted for selectively applying and relieving a measured pressure on a closed volume of fluid have been developed previously, such as for use in inflation of a balloon catheter used in angioplasty balloon procedures interiorly of blood vessels, or other types of balloon catheterization procedures.

Some examples of prior art devices for inflating and deflating a catheterized balloon device are disclosed in U.S. Pat. Nos. 4,838,864; 5,047,015; 5,168,757; 6,796,959 and 9,492,643.

The inflation device disclosed in U.S. Pat. No. 4,838,864 employs a threaded plunger and a release element constructed for selective threaded and unthreaded engagement with the threaded plunger. The plunger includes a handle for moving a piston within the device. However, the release element is not part of the handle, and therefore the device is not configured for single handed use.

The inflation device disclosed in U.S. Pat. No. 5,047,015 is unique in that it employs a plunger devoid of threads. Instead of the plunger including threads, the device employs a narrow, articulated thread bearing insert strip that is designed to deploy and engage surrounding mating threads. The narrow thread bearing insert strip relies, in part, upon force from a spring to maintain engagement under load. As such, a spring is called upon to bear the plunger's loading during pressurization. This is not ideal because the spring must be massive to withstand the plunger's load against it. For the plunger to handle a load from large pistons or high pressures devices, it must withstand plunger loadings of 300-500 lbF. The prior art device disclosed in the '015 patent is designed such that loading upon the plunger is actually borne by a narrow threaded insert which pushes against a spring and traverses diagonally toward the plunger's center. Plunger loading pushes the insert into a direction of disengagement rather than engagement (i.e., proximally and toward the center of the plunger). Therefore, a load placed upon the plunger must be resisted by a strong return spring. Furthermore, the thread must be designed to retract in a path that is neutral to its thread face angles such that it will not hang up or push the plunger distally (pressurizing direction) when being released from load as it traverses diagonally inward. Still further, this traversing angle must be one that provides the return spring a degree of mechanical advantage by wedging the thread insert outward. The thread must therefore be designed exactly reverse of ideal by having a greater sloped face, one that is parallel to its diagonal angle of retraction, to bear the pressurization load instead of the opposite thread face which is more perpendicular to the plunger's axis. For ideal load handling, such a thread design is completely contrary to best practice. As a result of the device employing a threaded insert rather than providing threads directly on the plunger, the device is not capable of withstanding substantial plunger loading. Given the geometric limitations of the thread insert (as discussed above), the only way for the strip to handle more pressure would be with a spring so large as to be impractical or impossible to manually operate.

U.S. Pat. Nos. 5,168,757; 6,796,959 and 9,492,643 disclose devices that provide improved syringing and pressurization control. All three patents are owned by the assignee of the present invention and are hereby incorporated herein in their entirety by reference. These patents disclose quick actuating mechanisms which enable rapid advancement of a plunger and alternatively allow user controllable threaded engagement of a screw thread bearing plunger to achieve precise control during final pressurization of a balloon catheter.

Both the '757 and '959 patents disclose similar devices that provide that a nut member is moved into and out of threaded engagement with a threaded plunger. The plunger has a handle, and the handle of the plunger and the actuating mechanism for engaging the nut member with the threaded plunger are separate mechanisms. As a result, neither one of the devices is configured for single hand use. Additionally, the devices have only a small surface area of thread engagement between the nut member and the threaded plunger, which results in more loading per thread compared to when there is a much larger surface area of engagement.

The '643 patent discloses a device that is configured for one handed operation. However, the device is similar to the devices disclosed in the '757 and '959 patents in that the device only provides for a small surface area of thread engagement.

SUMMARY

An object of an embodiment of the present invention is to provide a novel actuating mechanism for rapidly and selectively releasing or engaging a moveable threaded plunger, operable within a threaded member within a unitary syringe body.

Another object of an embodiment of the present invention is to provide a mechanism that is configured to control a high-pressure medical syringe for purposes of pressurizing, depressurizing and evacuating therapeutic medical balloon catheters, or the like.

Yet another object of an embodiment of the present invention is to provide a mechanism that provides for rapid manual reciprocation of a plunger, locking it in one place for precise thread controlled plunger advancement by means of plunger rotation as desired by the operator in order to either hold, displace, pressurize, depressurize or evacuate working fluid contained within a syringe.

Another object of an embodiment of the present invention is to provide a device that incorporates a threaded plunger design which provides a large surface area of thread engagement.

Still another object of an embodiment of the present invention is to provide a device that is configured such that operational loads between threaded members are transmitted directly by a plunger bearing a thread, and not indirectly through some intermediary component.

Briefly, an embodiment of the present invention provides a fluid displacement and pressurization device which provides both a substantial amount of thread engagement as well as provides for single hand control for all operational manipulations including maintaining a set fill volume, rapid filling and displacement, and pressurization and retention of evacuation positioning during balloon depressurization. The device allows for the use of one hand to not only transition the device from micro-movement control to macro-movement control, but also with regard to rotating, pushing or pulling the handle of the plunger.

The embodiment comprises a syringe body, a threaded plunger which extends into the syringe body, a threaded member inside the syringe body, control blades, a handle at an end of the plunger, and a control button in the handle. When the control button is not depressed, the control blades engage the threaded member with the threaded plunger. At that time, the handle of the plunger is rotatable to effect micro-movement of the plunger. The button in the handle is pressable to have the control blades disengage the threaded member from the threaded plunger inside the syringe body to allow for macro-movement of the plunger via pushing or pulling of the plunger into or out of the syringe body.

BRIEF DESCRIPTION OF THE DRAWINGS

The organization and manner of the structure and operation of the invention, together with further objects and advantages thereof, may best be understood by reference to the following description taken in connection with the accompanying drawings wherein like reference numerals identify like elements in which:

FIG. 11 is a cross-sectional view similar to FIG. 3, but relates to a second embodiment of the present invention, showing the device pressurized;

FIG. 12 shows a portion of FIG. 11 in more detail;

DESCRIPTION OF ILLUSTRATED EMBODIMENTS

Figure 1:
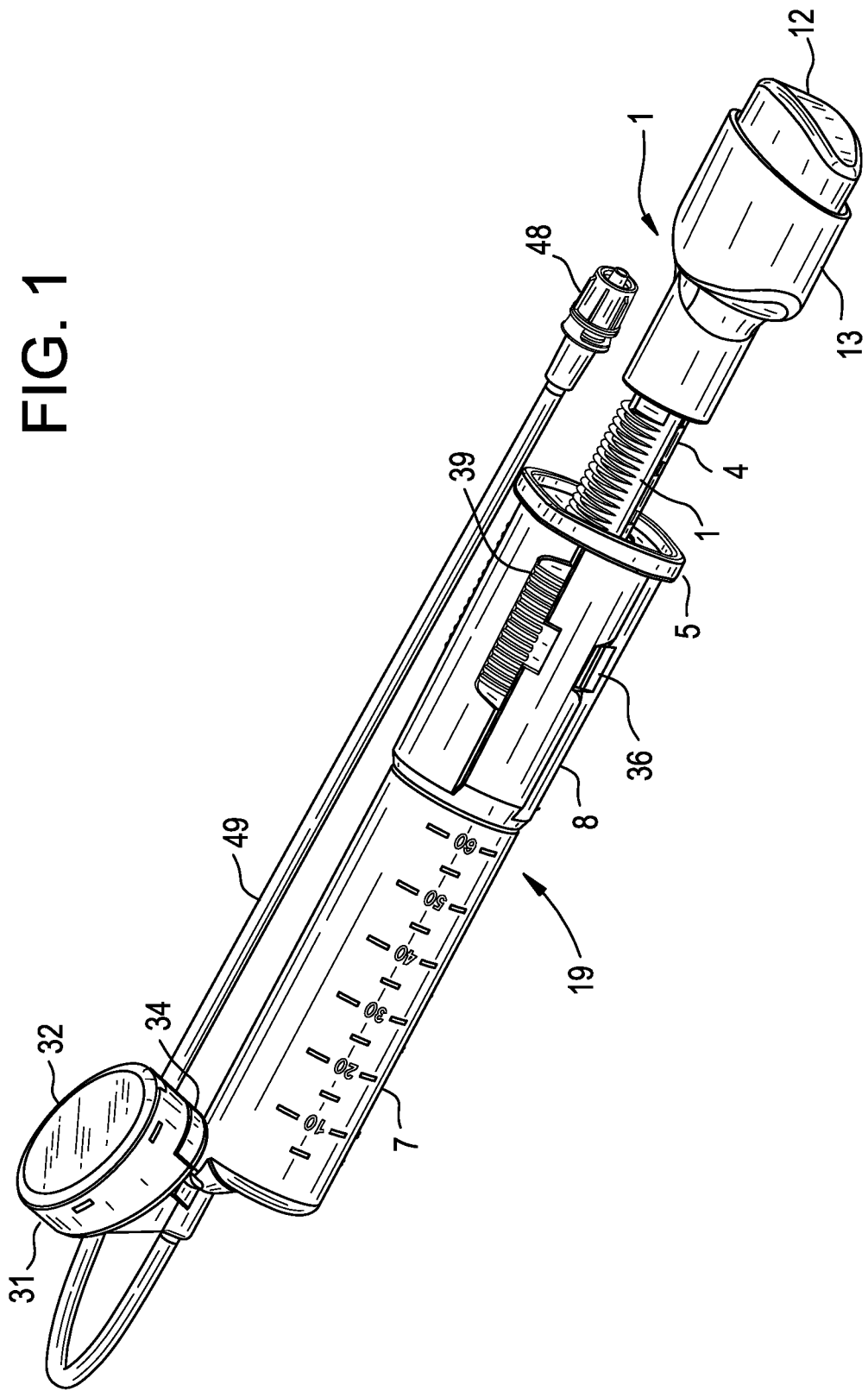
FIG. 1 is a perspective view of a fluid displacement and pressurization device which is in accordance with a first embodiment of the present invention.

While this invention may be susceptible to embodiment in different forms, there are shown in the drawings and will be described herein in detail, specific embodiments with the understanding that the present disclosure is to be considered an exemplification of the principles of the invention and is not intended to limit the invention to that as illustrated.

FIG. 1 illustrates a fluid displacement and pressurization device 19 which is in accordance with a first embodiment of the present invention. As shown, preferably the handle 13 of a plunger 1 is at one end of the fluid displacement and pressurization device 19 while the opposite end of the fluid displacement and pressurization device 19 is configured to engage a high pressure fluid delivery hose 49 (i.e., such as via a conventional hose-engaging socket). As shown, there may be a luer connector 48 at the end of the high pressure fluid delivery hose 49 that is connectable to, for example, a mating balloon catheter (not shown), or some other therapeutic medical device.

Preferably, the fluid displacement and pressurization device 19 includes a unitary syringe body 8 and the plunger 1 extends into the unitary syringe body 8. As will be described in more detail later herein, the fluid displacement and pressurization device 19 is configured such that the plunger 1 is translatable relative to the unitary syringe body 8, either by pushing or pulling on the handle 13 of the plunger, or by rotating the handle of the plunger. Translation of the plunger results in pressurization or depressurization of the mating balloon catheter (or other therapeutic medical device) that is connected to the luer connector 48 at the end of the high pressure fluid delivery hose 49.

Preferably, the unitary syringe body has a barrel 7 and is entirely transparent (at least at the barrel 7) to monitor the volume of working fluid within the barrel 7 and facilitate both fluid filling and purging of trapped and entrained air in preparation for use. As shown in FIG. 1, the barrel 7 may have volume indicia thereon.

Typically, medical fluid pressurization devices such as those disclosed in the prior art patents referenced above are equipped with pressure monitoring features. Most commonly, they are equipped with traditional mechanical pressure gauges. These types of self-contained pressure gauges generally have their own threaded spigot, protective case and lens and they are most often secured to the device by means of threaded sockets or snap ring retaining features. Additionally, they must often be held in place with a bonding agent regardless of their primary retaining means in order to prevent rotation during use.

In contrast, preferably the medical fluid pressurization device 19 disclosed herein is equipped with a pressure monitoring feature in the form of gauge module 30. Preferably, the gauge module 30 comprises the most elemental component of a mechanical gauge, simply comprised of a bourdon tube, clockwork mechanism, indicator needle, dial face and fluid communication port. Preferably, it is not equipped with any form of threaded socket, housing or protective lens and does not require use of any bonding agent to prevent rotation once installed.

Instead, preferably a gauge housing 31 protects the working elements of the gauge module 30, and the gauge housing 31 is preferably provided as an integral feature of the unitary syringe body 8. Preferably, as shown in FIG. 2, the gauge module 30 is secured within this housing 31 by means of self-tapping retaining screws 33, and a lens 32 is configured to snap in place onto the gauge module housing 31 to protect the dial face of the gauge module 30.

As shown In FIG. 1, the fluid displacement and pressurization device 19 includes a control button 12, and the control button 12 is preferably provided at the end of the fluid displacement and pressurization device 19, in the handle 13 of the plunger 1. As will be described in more detail later hereinbelow, depressing the control button 12 transitions the fluid displacement and pressurization device 19 from micro-movement control (i.e., achieved by rotating the plunger handle 13) to macro-movement control (i.e., achieved by pushing or pulling the handle 13 so the plunger 1 translates either further into or further out of the unitary syringe body 8).

Figure 2:
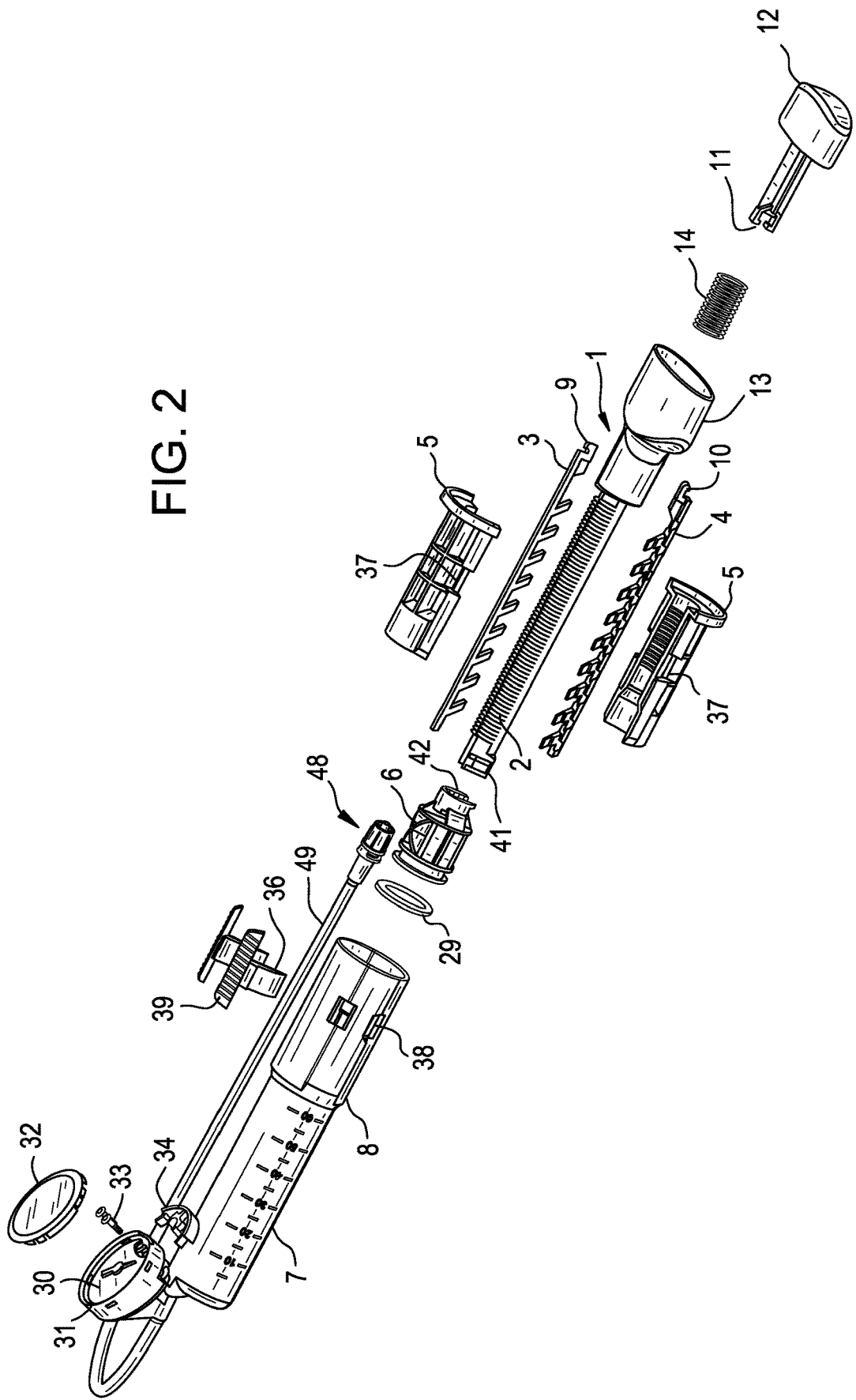
FIG. 2 is an exploded perspective view of the fluid displacement and pressurization device shown in FIG. 1.

FIG. 2 provides an exploded view of the fluid displacement and pressurization device 19. As shown, the fluid displacement and pressurization device 19 also includes a threaded member 5 preferably in form of a threaded cylinder, a plurality of control blades (specifically a thread control blade 3 and a thrust control blade 4), a spring 14, a pair of locking keys 36, a piston 6, and a sealing ring 29 that is preferably in the form of a rubber o-ring.

Figure 3:
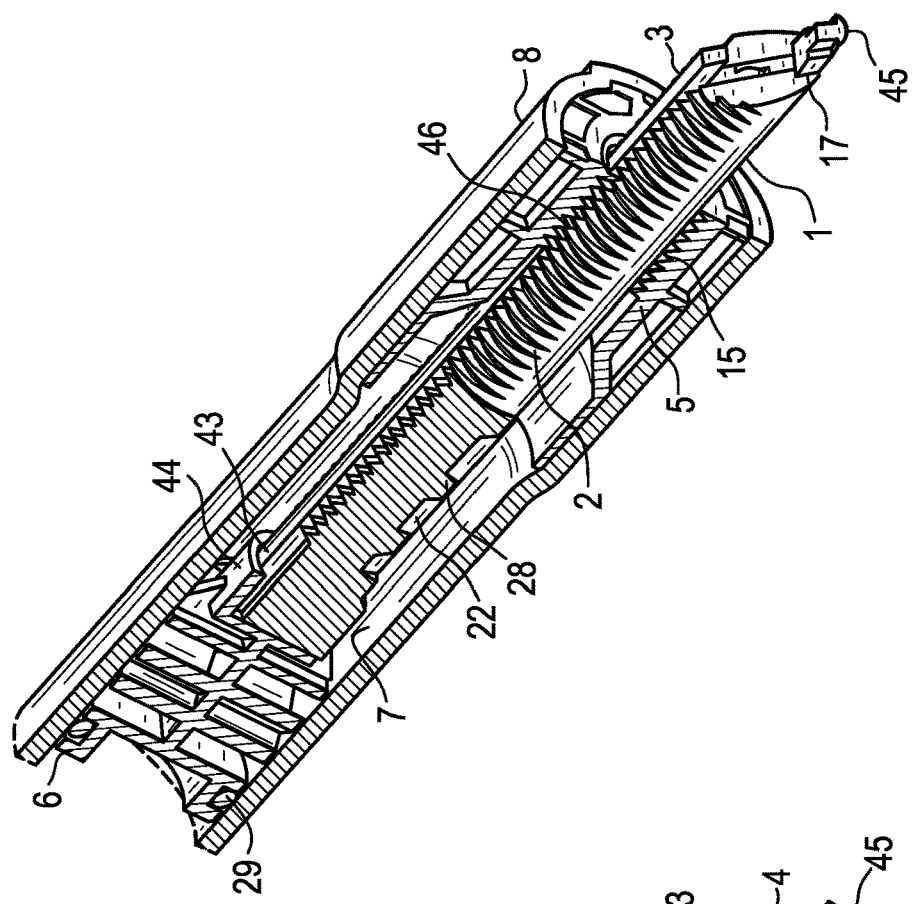
FIG. 3 is a cross-sectional view of a portion the device shown in FIGS. 1 and 2, showing a plunger locked into threaded engagement with a threaded cylinder.
Figure 4:
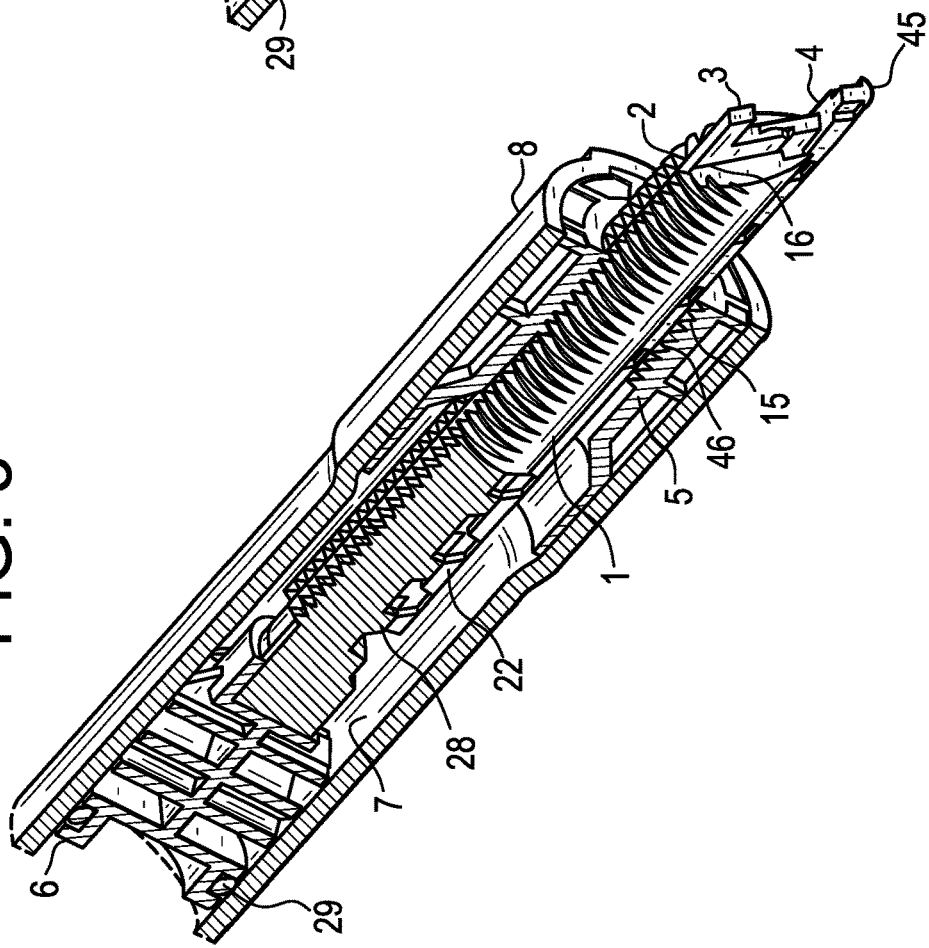
FIG. 4 is similar to FIG. 3, but shows the plunger moved out of threaded engagement with the threaded cylinder.

As shown in FIGS. 3-9, the piston 6 is engaged with the end of the plunger 1, and the sealing ring 29 is disposed on the piston 6 and (as shown in FIGS. 3 and 4) seals against an internal wall of the barrel of the unitary syringe body 8.

The unitary syringe body 8 is configured to retain the threaded cylinder 5 to guide and engage the plunger 1 which is operable within it. The plunger 1 preferably includes a fixed thread 2 along its entire working length.

This disclosure describes a fluid displacement and pressurization device 19 which includes a novel actuating mechanism for rapidly and selectively releasing or engaging a moveable threaded plunger 1 operable within a stationary internally threaded cylinder 5 within a unitary syringe body 8. This mechanism is particularly suited to control a high-pressure medical syringe for purposes of pressurizing, depressurizing and evacuating therapeutic medical balloon catheters, or the like. The mechanism includes a threaded plunger 1 having a piston 6 installed at one end to traverse the barrel portion of the unitary syringe body 8, a handle 13 with a control button 12 at the other end of the plunger 1 (i.e., opposite the piston 6) and means provided within the plunger 1 to allow an operator to selectively engage and disengage the threaded plunger 1 from the threaded cylinder 5 by operating a control button 12 located within the plunger 1. This mechanism provides for rapid manual reciprocation of the plunger 1, locking it in one place, or precise thread controlled plunger advancement by means of plunger rotation as desired by the operator in order to either hold, displace, pressurize, depressurize or evacuate working fluid contained within the syringe.

The fluid displacement and pressurization device 19 provides that the plunger 1 is threaded and the plunger 1 is simply driven into engagement by the thrust control blade 4 which first traverses axially until its cam follower clears the cam and then moves inward toward the plunger's center to relieve plunger thread engagement. That complex motion would not be possible with a threaded insert.

Unlike the prior art syringe devices referenced in the United States patents previously cited, the fluid displacement and pressurizing inflation device 19 disclosed herein and shown in FIG. 1 utilizes a novel, user selectable plunger control mechanism that does not rely upon any form of moving half-nuts, retracting and emerging thread bearing insert strips within the plunger or expanding threaded segments. This mechanism as shown in FIG. 2 instead, utilizes a rigid, load bearing plunger 1 having a fixed thread 2 along its entire working length and a pair of control blades 3 and 4 whose outer edges are parallel to the longitudinal axis of plunger 1 and are configured to make the thread 2 of the plunger 1 selectively engageable or disengageable with the thread 15 in the threaded cylinder 5. The control blades 3 and 4 are positioned to selectively drive, maintain or facilitate the release of threaded engagement between the thread 2 on the plunger 1 and the thread 15 (see FIGS. 3 and 4) within the threaded cylinder 5.

The control blades 3 and 4 are able to either lock plunger 1 and its attached piston 6 in a desired position within the syringe barrel bore 7 of the unitary syringe body 8 and provide for thread assisted micro-movement, or release this engagement to allow macro-movement. Once the plunger 1 is locked (as shown in FIG. 3, which is sectioned off center to better show features) into threaded engagement with the threaded cylinder 5, precisely controlled micro-advancement and retraction of the plunger 1 becomes available by means of plunger rotation (i.e., by rotating the handle 13). On the other hand, whenever the control button 12 is depressed (see FIG. 5), the control blade 3 releases and prevents engagement of the plunger thread 2 with the thread 15 of the threaded cylinder 5 (as shown in FIG. 4, which is sectioned off center to better show features) in order to facilitate free macro-movement of the plunger 1 (i.e., by pushing or pulling on the handle 13).

Figure 6:
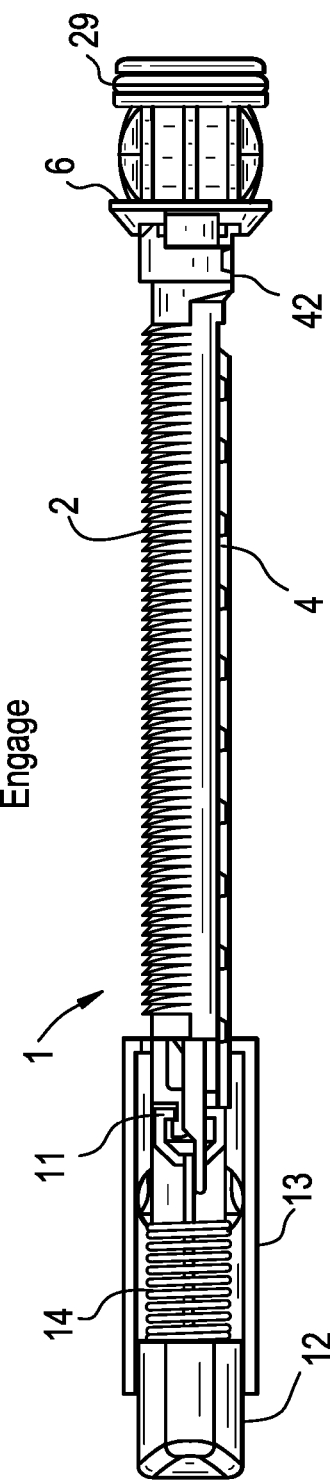
FIG. 6 is similar to FIG. 5, but shows the components when the button on the end of the fluid displacement and pressurization device is not depressed.

The control blades 3 and 4, generally positioned 180° from one another and along the entire threaded length of plunger 1, are preferably provided with tabs 9 and 10 to engage hooks 11 of the control button 12 residing within the handle portion 13 of plunger 1. Further, as shown in FIG. 6, control button 12 contains a spring 14 that bears against the handle 13 in order to drive the control button 12 outward and thereby place the control blades 3 and 4 in position to maintain threaded engagement of the plunger 1 with the thread 15 of the surrounding threaded cylinder 5.

Figure 7:
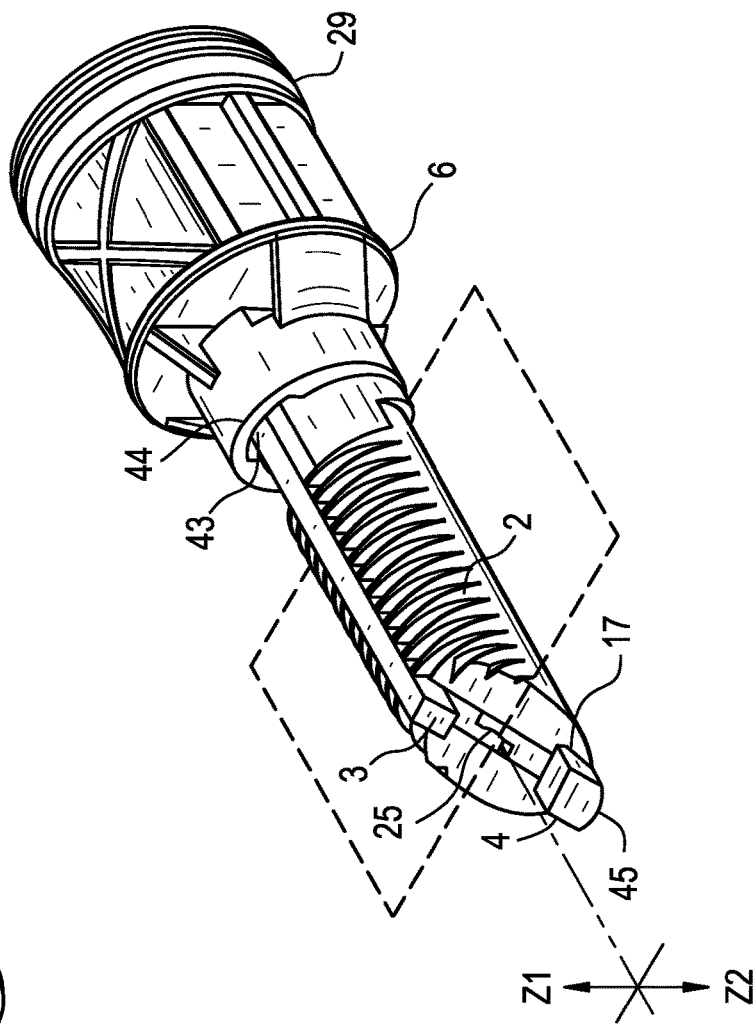
FIGS. 7 and 8 together effectively show movement of control blades during operation of the fluid displacement and pressurization device.

The control blades 3 and 4 each contain unique and specialized features peculiar to the purpose they serve as well as some common features, and each resides within its own dedicated and unique longitudinal guide groove within the plunger 1. Specifically, as shown in FIG. 7, the thrust control blade 4 is positioned opposite the thread 2 on the plunger 1 and operates within guide groove 17. On the other hand, the thread control blade 3 is positioned along the center of the thread 2 on the plunger 1 and operates within guide groove 16. Preferably, both control blades 3 and 4 are designed to translate transversely outward from the plunger 1 for a distance equal to the depth of the thread 2 in response to the position of the control button 12.

Figure 8:
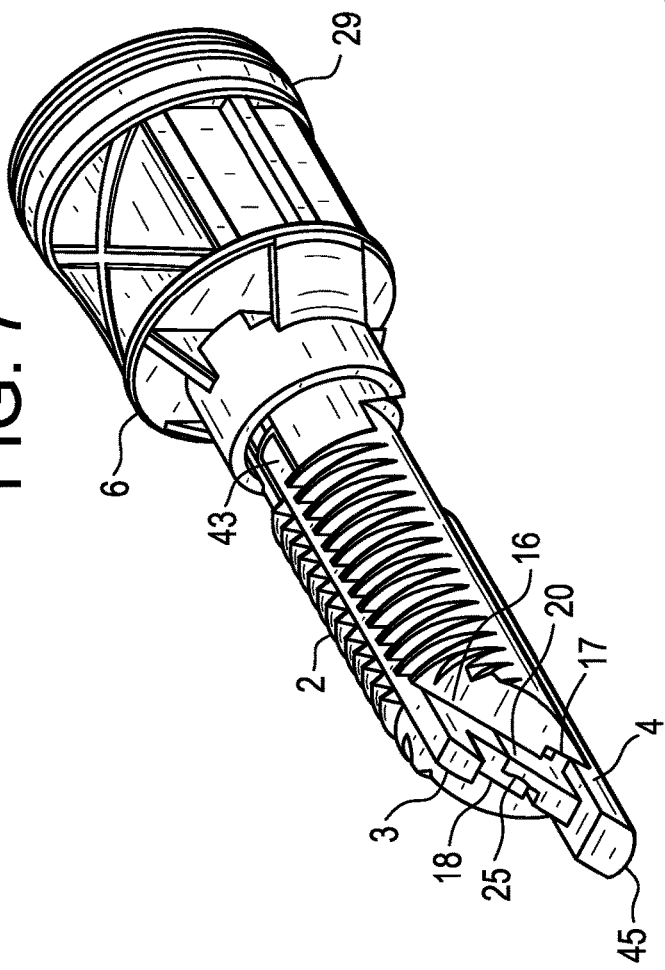

As shown in FIG. 8, the shaft of the plunger 1 is geometrically divisible into two zones (Z1 and Z2) by a longitudinal geometric plane (shown in FIG. 8 using a dashed line) disposed through the longitudinal axis, wherein a first zone (Z1) of the two zones is provided with said thread 2 of the plunger 1 and a second zone (Z2) of the two zones contains no thread.

Preferably, the control blade 3 is simpler than control blade 4 and effectively has four functions, namely: a) to assist the release of plunger thread 2 from threaded engagement with mating thread 15 on the threaded cylinder 5; b) to prevent undesired re-engagement of these threads; c) to shift the rotational axis of the plunger 1 out of alignment with the center axis of the threaded cylinder 5 during disengagement from the thread 2 on the plunger 1 from the thread 15 in the threaded cylinder 5; and d) to shift the rotational axis of the plunger 1 out of alignment with the center axis of the piston 6 that is at the end of the plunger 1.

The shift of the rotational axis of the plunger 1 away from alignment with the center axis of the threaded cylinder 5 is initiated by user compression of the control button 12 and is accommodated by a transversely sliding coupling provided between the distal end of plunger 1 and piston 6. This coupling consists of a "T" shaped feature 41 at the distal end of plunger 1 that engages a mating T-slot receptacle 42 at the proximal end of piston 6 (as used herein, the term distal refers to a point furthest from the operator while the term proximal refers to a point nearest the operator). The off-axis shift, driven by the thread control blade 3 pushing against the closed end 44 of piston T-slot receptacle 42, is necessary because the plunger 1 in its entirety must be shifted transversely, by an amount equal to the depth of the plunger thread 2, in order to disengage the plunger thread 2 from the thread 15 of the threaded cylinder 5.

Figure 5:
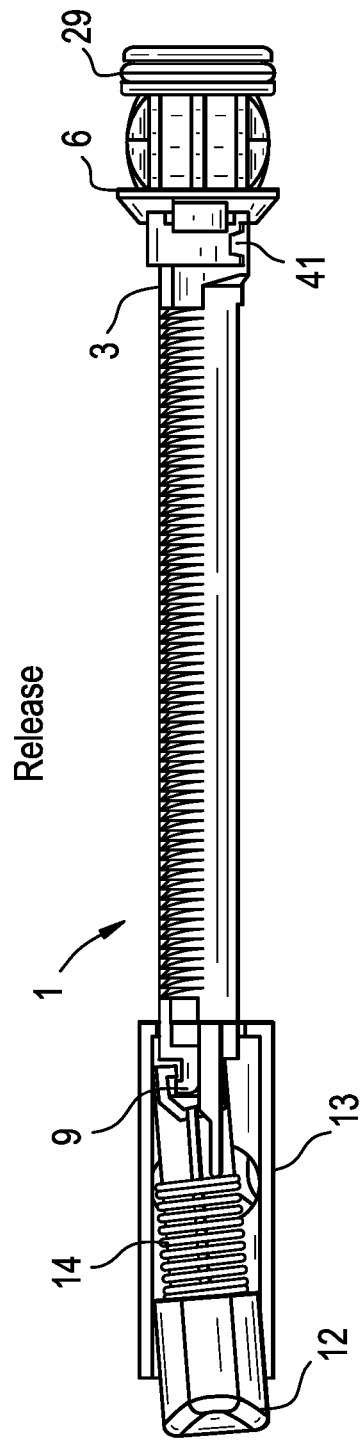
FIG. 5 shows certain components of the fluid displacement and pressurization device when a button on an end of the fluid displacement and pressurization device is depressed.

As shown in FIG. 8, a lifter tip 43 is located at the tip of the control blade 3, and is positioned to drive this transverse shift between the plunger 1 and the piston 6 whenever the lifter tip 43 pushes the "T" shaped feature 41 of the plunger 1 away from the closed end 44 of the T-slot receptacle 42. This off axis shift of the plunger 1 relative to the position of control blades 3 and 4 must also be accommodated by the control button 12, as shown in FIG. 5. The control button 12, while being contained within the plunger handle 13, is not constrained to strict longitudinal axial movement. Instead, the control button 12 is configured to float within the confines of the plunger handle 13 and therefore remain attached to, and track along with, the control blades 3 and 4 whenever the plunger 1 shifts from an on-axis position with threads 2 and thread 15 engaged to an off-axis position whenever control button 12 is depressed to disengage the threads.

Conversely, the restoration of axial alignment between the plunger 1 and the center axes of the thread 15 and piston 6 occurs when thrust control blade 4 pushes against the tips 46 (see FIGS. 3 and 4) of thread 15. Whenever the control button 12 is released after having been depressed, the thrust control blade 4 (the more complexly configured of the two control blades 3 and 4) pushes outward, away from the center of the plunger 1 as shown in FIG. 3, thereby withdrawing the thread control blade 3 inward, toward the center of the plunger 1. This action shifts the center axis of the plunger 1 into concentric alignment with the center axis of the piston 6 and thread 15 thereby driving the thread 2 of the plunger 1 into locking engagement with mating thread 15 as thread control blade 3 withdraws toward the center of the plunger 1 (shown in FIG. 3). Once deployed, the control blade 4 also serves to counter the side thrust generated by these mated threads when they are under load, such as when the plunger 1 is rotated to drive the piston 6 distally into the cylinder bore 7 to working pressure within inflation device 19. The control blade 4 is preferably provided with a wide bearing surface 45 which delivers side thrust of the mated threads under load to the tips 46 of thread 15. The transverse shift of the plunger 1 resulting from the action of the control blade 4 during operator release of the control button 12 is accommodated by the slidable coupling between T-slot receptacle 42 of the piston 6 and the T-shaped feature 41 that is located at the distal end of the plunger 1. Because the thrust control blade 4 and the thread control blade 3 operate synchronously with one another, upon operator release of control button 12, the lifter tip 43 simultaneously withdraws away from the closed end 44 of the piston T-slot receptacle 42.

In order to assure the synchronous operational relationship between control blades 3 and 4, the thread control blade 3 and the thrust control blade 4 are preferably joined to one another by interlocking features 25 which are provided at the ends of a series of angled fingers 18 and 20 (shown in FIGS. 7 and 9), depending from blades 3 and 4, respectively. Interlocking of the angled fingers 18 and 20 assures that the opposing blades operate in unison whenever they are acted upon by the control button 12. These joinable fingers are mated into an interlocked relationship when both control blades 3 and 4 are fully inserted into their designated guide grooves 16 and 17 and their respective angled fingers 18 and 20 meet within the array of angled receiving slots 21 (see FIG. 10) provided for them within the plunger 1. The receiving slots 21 are preferably configured with sufficient clearance and resilience for the interlocking features 25 of the angled fingers 18 and 20 to bypass one another when sufficient compressive assembly force has been applied to the outer edges of each control blade, whereby they become engaged. Once snapped together within the close-fitting confines of receiving slots 21, preferably the interconnections of the angled finger's interlocking features 25 are maintained by the close fit of the finger receiving slots 21 through which they were initially inserted.

Solid webs 40 of plunger 1 that separate each of the finger receiving slots 21 and join guide grooves 16 and 17, run parallel to the interlocked angled fingers 18 and 20 of control blades 3 and 4. The proximal and distal edges 24 and 23 of the solid webs 40 form the boundaries of the receiving slots 21 and serve as ramps upon which the distal and proximal edges 27 and 26, respectively, of the assembled angled fingers 18 and 20 are guided during movement, whenever the control blades 3 and 4 are moved longitudinally fore or aft, i.e., along the axis of the plunger 1.

Figure 9:
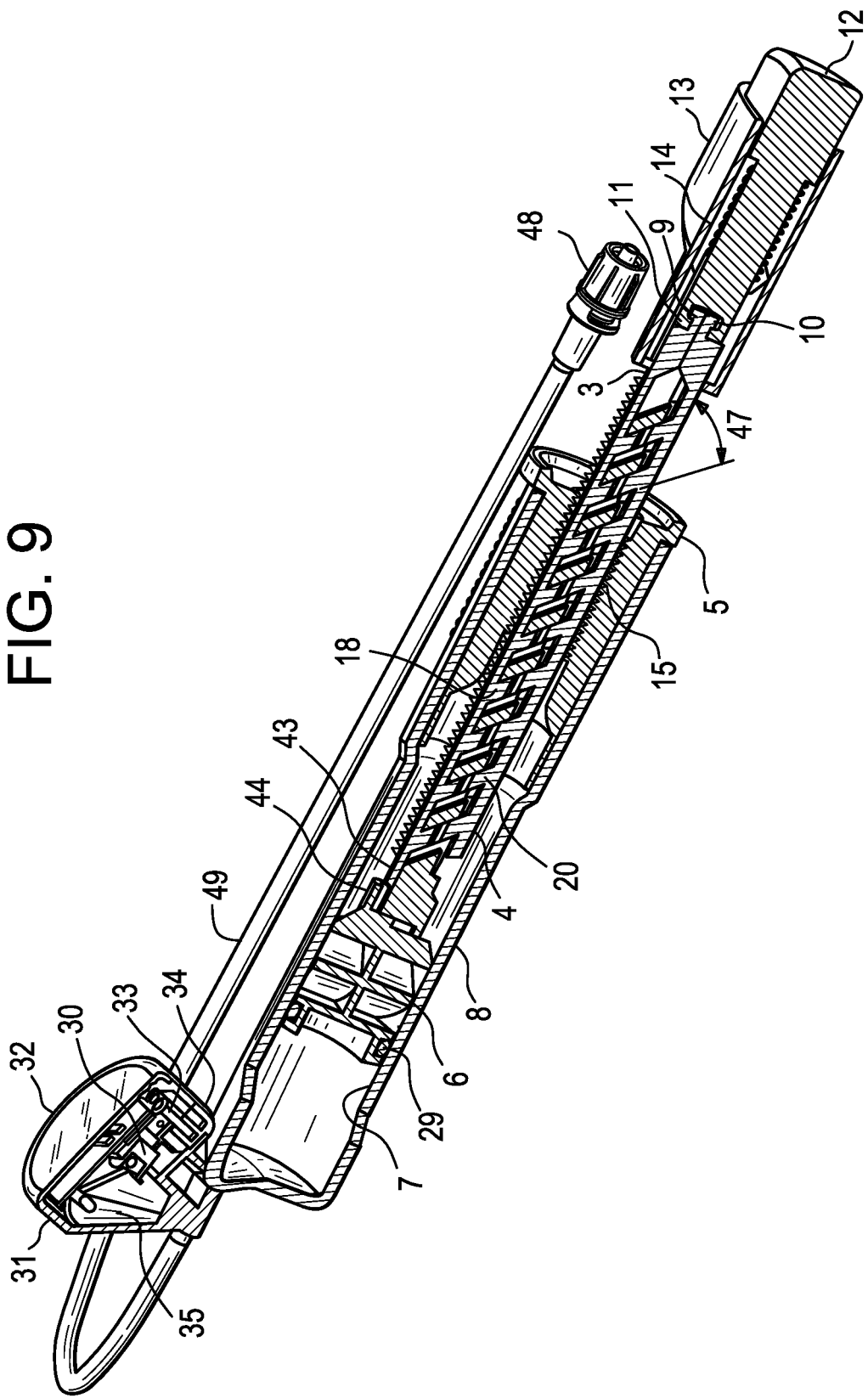
FIG. 9 is a cross-sectional view of the fluid displacement and pressurization device shown in FIGS. 1 and 2.
Figure 10:
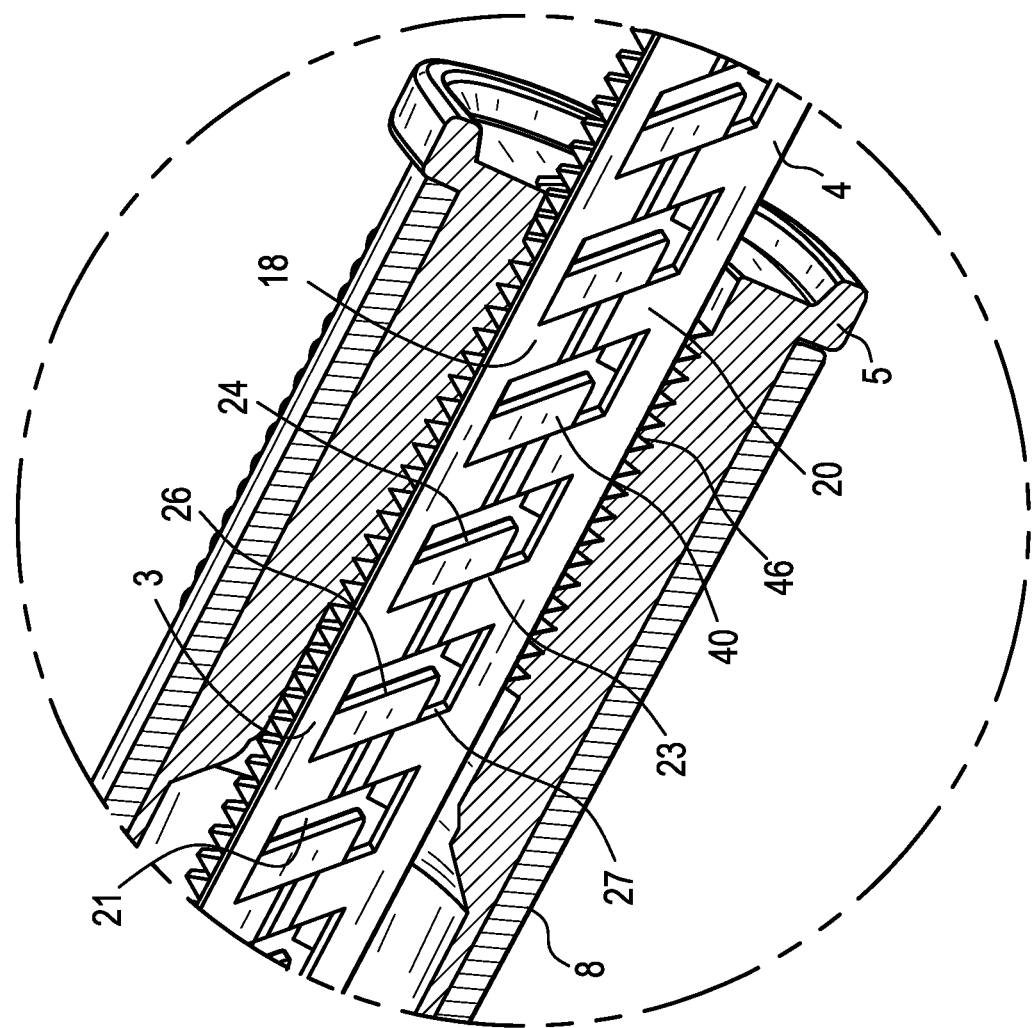
FIG. 10 is an enlarged view of a portion of that which is shown in FIG. 9.

The angle (as shown in FIG. 9) at which the interlocked angled fingers 18 and 20 are arrayed, finger angle 47, determines the amount of transverse displacement obtainable by the control blades 3 and 4 to disengage the plunger thread 2 from the thread 15 in the threaded cylinder 5, in response to longitudinal operator applied movement of the control button 12.

Choice of this angle is driven by the output response desired for a given operator input. Finger angle 47 can preferably range from 22.5° to 67.5°, with an angle close to 45° being most preferred. Positioning the angled fingers 18 and 20 and their respective finger receiving slots 21 at 45° to the plunger's longitudinal axis, for example, will produce a translational movement of the control blades 3 and 4 that is transversely equal to the longitudinal movement of the control button 12 and (notwithstanding friction or the force of control button spring 14) requires a button input force equal to the side thrust developed by plunger thread 2 while under load. An angle more acute than 45°, for example one such as 22.5° to the axis of the plunger 1, would (notwithstanding friction and the force of spring 14) require a user force upon control button 12 equal to one half of the side thrust presented by the plunger 1 when under load but also require twice the longitudinal movement of the control button 12 to obtain the necessary transverse translational movement of the control blades 3 and 4. An angle less acute than 45°, for example one such as 67.5° to the axis of the plunger 1, would (notwithstanding friction and the force of spring 14) require a user force upon control button 12 equal to one and one half of the side thrust presented by the plunger 1 when under load, but also require two thirds the longitudinal movement of the control button 12 to obtain the necessary transverse translational movement of the control blades 3 and 4. The angular disposition of angled fingers 18 and 20 and receiving slots 21 therefore, may be chosen to accommodate user expectations or requirements. Other factors impacting choice of this angle are the quantity of interconnecting angled finger necessary to locally support the thrust blade 4 when the plunger 1 is placed under a pressurization load, the width of the angled fingers 18 and 20, and the size of webs 40 required to meet plunger strength requirements.

In order to allow the spring 14 to be light enough for comfortable use, it must be isolated from the reactionary load forces upon thrust control blade 4 that occur whenever plunger threads 2 are under working load during pressurization of the device. Therefore, as best shown in FIG. 3, preferably there is a guide groove 17 on the plunger 1 which provides a series of thrust blade control cams 28, and preferably thrust blade 4 contains a series of cam followers 22, properly positioned to ride up onto and bear against mating thrust blade control cams 28. This arrangement of cams and cam followers provides rigid local support to thrust control blade 4 at a location adjacent to bearing surface 45 while in contact with the thread tips 46 of the threaded cylinder thread 15. The plunger 1 is thereby placed under transverse compression, which in turn eliminates the need for the spring 14 to bear any reaction load received by the thrust control blade 4 when the plunger 1 is placed under load during device pressurization.

During pressurization of the inflation device 19, the threaded cylinder 5 is relied upon (through the rotational engagement of the plunger thread 2 within the thread 15 of the threaded cylinder 5) to drive plunger 1 (and therefore also piston 6 and pressure seal 29) distally along the syringe barrel bore 7. The force of the plunger 1 against the threaded cylinder 5 resulting from this type of pressurization attempts to drive the threaded cylinder 5 proximally toward the operator. Therefore, means must be included to anchor the threaded cylinder 5 to the unitary syringe body 8 and transfer the resulting load of thread driven pressurization, directly to the unitary syringe body 8.

To this end, locking keys 36 are preferably utilized to engage locking key notches 37 of the threaded cylinder 5 with corresponding locking key receiving ports 38 provided along the sides of the unitary syringe body 8. The locking keys 36 are preferably configured to snap rigidly into place within the locking key receiving ports 38 of the unitary syringe body 8. The locking keys 36 can also provide the ideal platform for incorporation of additional features, such as locking key mounted grips 39 as shown in FIG. 2. Grips of this simple type (or even larger and more complex handle forms) can be included to allow users to grasp the inflation device 19 securely during operation and handling.

The bodies and barrels of the type of pressurizing syringes disclosed herein can be made from a variety of proprietary resins but they are most typically manufactured from commonly available, injection moldable polycarbonate resins which have high transparency, high impact resistance, superior strength compared to most other transparent resins and reasonable cost in light of their performance properties. The use of convenient self-tapping screws however, often poses design challenges for assemblies formed of these engineering resins due to internal stresses within the resin created by such fasteners. One critical weakness of polycarbonate resin is its inability to withstand the prolonged stress under load that generally accompanies the use of self-tapping fasteners. Therefore, polycarbonate resin is often an undesirable resin choice whenever the use of self-tapping screws is desired. In such instances, alternate materials often of higher cost and lower strength may be employed, but utilizing these alternatives generally forces designers to accept the less desirable compromises of material properties and cost. The design of an embodiment of the present invention (and its intended performance characteristics) make polycarbonate resin the material of choice. However, in order to allow the use of self-tapping retaining screws 33 to secure the gauge module 30, an alternative solution is required. One option would be to mold screw threads into the gauge receiving structure 35 but molding small screw threads into this type of component requires very complex, costly and maintenance intensive mold construction. Another alternative (the one disclosed previously herein), is employment of a gauge module retaining insert 34 made from a material such as ABS, nylon, copolyester or the like including reinforced varieties of these materials for example that are tolerant of stress from self-tapping screws. This insert, when formed of such materials can be robust and unaffected by the stress of a self-tapping screw. A gauge module retaining insert 34, therefore allows the use of an otherwise desirable material such as polycarbonate resin for the main body of inflation device 19. Beyond providing an anchor for self-tapping screws, the gauge module retaining insert 34 can serve as part of the protective gauge housing. Additionally, because it is manufacturable in a variety of colors, the gauge module retaining insert 34 can also serve as a unique decorative and differentiating feature for inflation device 19.

Benefits to the user of a device of this construction include single hand control of the plunger 1 for all operational manipulations including maintaining a set fill volume, rapid filling and displacement, screw thread assisted pressurization and retention of evacuation positioning during balloon depressurization. Unlike prior art devices such as the one described in U.S. Pat. No. 5,047,015, actuation of device control by means of the plunger mechanism is easily achieved when performing any of the intended use procedures because the control button's return spring 14 is not called upon to bear any of the plunger's loading during pressurization. This device construction is also capable of delivering to the piston 6 and sustaining very high plunger force loading and yet do it with comfortable user control input. The threaded plunger design of this device provides a large surface area of thread engagement (for example, more than twice the surface area of the applicant's previously discussed prior art devices), and therefore enjoys much lower loading per unit of thread surface area. Further, because the plunger threads 2 are part of the plunger 1, operational loads between the piston 6 and the device housing's threaded member 5 engaging the plunger 1 are transmitted directly by the plunger 1 and not indirectly through an attached component as would be the case with a threaded insert strip. Plunger loading in excess of 300 LbF and potentially higher than 500 LbF are thereby possible, allowing large displacement high pressure devices to be built to service the needs of new improved therapeutic procedure balloons.

Figure 14:
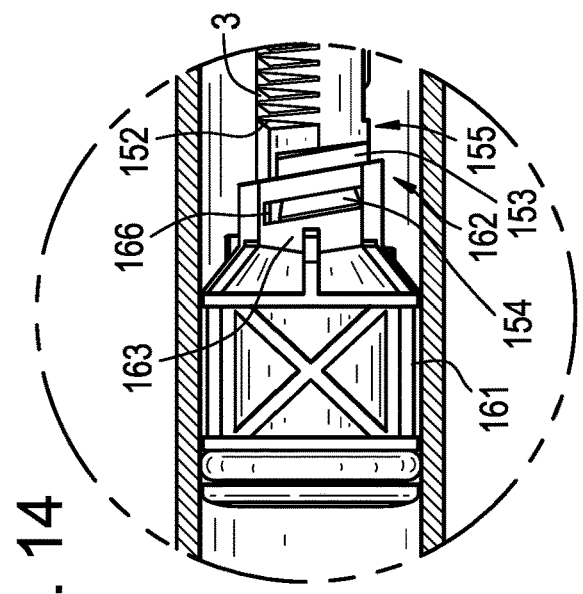
FIG. 14 shows a portion of FIG. 13 in more detail.
Figure 13:
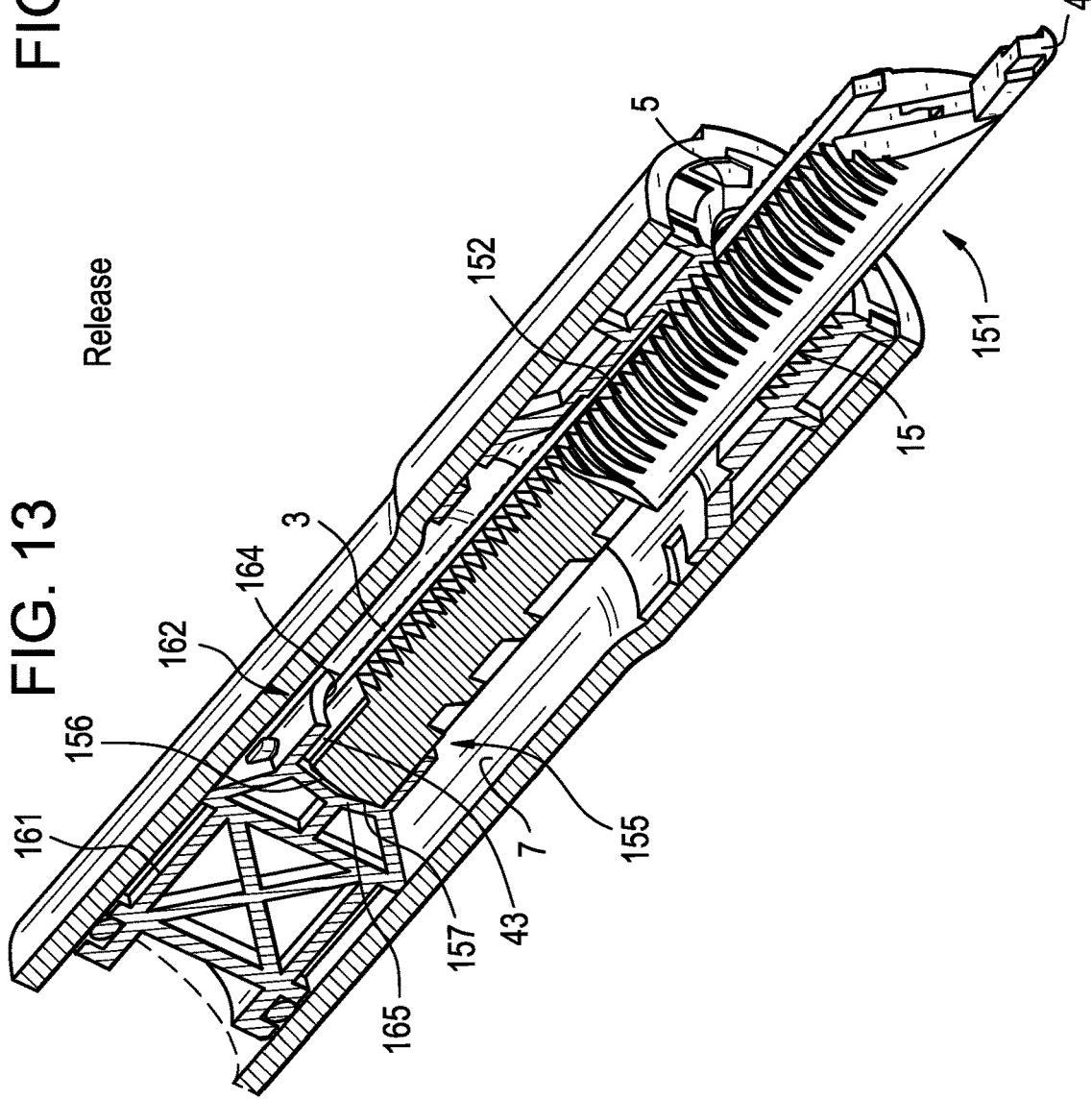
FIG. 13 is a cross-sectional view similar to FIG. 4, but relates to the second embodiment of the present invention, showing the pressure released.

FIGS. 11-14 relate to a second embodiment of the present invention. Specifically, FIG. 11 is a cross-sectional view that is similar to FIG. 3, showing the device pressurized, and FIG. 13 is a cross-sectional view that is similar to FIG. 4, showing the pressure released. FIG. 12 and FIG. 14 each show a portion of FIGS. 11 and 13, respectively, in more detail.

The embodiment shown in FIGS. 11-14 is very similar to the previous embodiment, so only the differences will be described and like part numbers will be used to identify like parts. For example, like the first embodiment shown in FIGS. 1-10, the second embodiment shown in FIGS. 11-14 includes thread control blades 3 and 4, a threaded cylinder 5 having a thread 15, a control button 12, angled fingers 18 and a lifter tip 43.

Compared to the first embodiment, the second embodiment is the preferred embodiment and includes both an improved plunger 151 and improved piston 161. The improvements provide an improved interface which greatly enhances user control, as well as provides better plunger to piston stability for improved seal performance and allows higher plunger loading.

Compared to the first embodiment shown in FIGS. 1-10, the second embodiment shown in FIGS. 11-14 provides better centralization of the plunger 151 within the piston 161 during device pressurization, particularly when the plunger's threads are engaged and loaded against the threaded cylinder element 5. Better centralization serves to ensure more uniform seal loading for higher pressure seal performance. As previously disclosed, the plunger's thread 2 is driven transversely into engagement with the threaded cylinder 5 by the thrust control blade 4 and this thrust control blade 4 thereby both establishes and aligns the engaged plunger's rotational axis with the piston's central axis. The improved plunger to piston interface associated with the embodiment shown in FIGS. 11-14 relives plunger side loading of the piston 161 by the thrust control blade 4 during device pressurization (shown in FIGS. 11 and 12), provides for reduced transitional release travel of the thread control blade 3 against the piston 161 during device depressurization (shown in FIGS. 13 and 14) and assures that the rotational axis of the plunger 151 remains parallel to the common axis of the device throughout its transverse movement. Additionally, this interface assures mutual axial alignment of the piston 161 and plunger 151 during pressurization (shown in FIGS. 11 and 12) and more precise alignment of the plunger 151 with the threaded cylinder 5 while they are engaged. The rigidity of the improved piston to plunger interface that is provided by the second embodiment is further enhanced when working fluid pressure, generated during device operation, compresses the individual components tightly together thereby causing them to behave as a solid unit rather than two separate components. While the improvement associated with the second embodiment involves the plunger and piston elements of the device, the functionality of these improved components still relies on interaction with components that remain unchanged with regard to the first embodiment. The basic function and operation between the two embodiments remain unchanged, as will become clear in the following discussion.

Much like the first embodiment, the second embodiment provides that plunger thread disengagement results from shifting the rotational axis of the plunger out of alignment with the center axis of the threaded cylinder 5 when a user compresses control button 12 and thereby causes the thread control blade 3 to extend outward and the thrust control blade 4 to simultaneously withdraw inward. With regard to the second embodiment, shifting the rotational axis of the plunger 151 with the piston 162 is accommodated by a transversely slidable connection between a distal tip 155 of the plunger 151 and a proximal end of the piston 161. As best shown in FIGS. 11 and 12, the improved piston to plunger connection relies upon a distal receptacle sleeve 162 of piston 161, wherein the receptacle sleeve 162 is preferably of a tubular configuration having parallel flat sidewalls 163 joined by semicircular walls 164 which receive the distal end of the plunger 151. As shown, preferably each of the parallel flat sidewalls 163 of the receptacle sleeve 162 is provided with matching angularly disposed receptacle slots 166. As shown in FIG. 11, preferably the bottom of the receptacle sleeve 162 is configured with a plunger centering feature in the form of a centrally located symmetrical pair of planar faced angled ramps 165 at the base of the receptacle sleeve 162. These angled ramps 165 are preferably arranged such that the minor included angle between their planar faces is ideally equal to but no less than twice the thrust face angle 159 of the plunger thread 152.

Preferably, the distal tip 155 of the plunger 151 is equipped with a pair of flat parallel sides 153 to closely fit receptacle sleeve 162 and both are provided with angled retention barbs 154 to engage and retain into the angled receptacle slots 166 of receptacle sleeve 162. Preferably, the distal tip 155 of the plunger 151 is further equipped with two angularly disposed planar surfaces as shown in FIG. 11, comprising an abutment plane 156 and a sliding guide plane 157, both being arranged to intimately align with and engage the angled ramps 165 within the receptacle sleeve 162. These two angularly disposed planar faces are preferably oriented perpendicular to the flat parallel sides 153 of the plunger 151 and are preferably symmetrically arrayed about the rotational axis of the plunger 151, wherein the axis is established when the plunger thread 152 is engaged with the thread 15 of the threaded cylinder 5. The two planar end faces of the distal tip 155 of the plunger 151 are preferably further arranged with the abutment plane 156 adjoining the edge of the plunger 151 containing the thread control blade 3 and the sliding guide plane 157 adjoining the edge of the plunger 151 opposite the thread control blade 3. The abutment plane 156 and the sliding guide plane 157 are preferably symmetrically disposed at an included angle centered upon the rotational axis of the plunger 151, an angle that is ideally equal to, but no less than, the thrust face angle 159 of the plunger thread 152. The ideal included angle between abutment plane 156 and the sliding guide plane 157 is therefore equal to, but not less than, twice the thrust face angle of the plunger thread 152 and in all instances identical to the included angle between the angled ramps 165 upon which they intimately engage.

In operation, pressing the control button 12 causes the thread control blade 3 (with lifter tip 43) to extend transversely in order to release the plunger thread 152 from engagement with the thread 15 of the threaded cylinder 5. The resulting transverse movement of the lifter tip 43 pushes the plunger 151 away from the semicircular wall 164 of the piston receptacle sleeve 162 as shown in FIGS. 13 and 14, thereby causing the end of the distal tip 155 of the plunger 151 to traverse within the piston receptacle sleeve 162 and move out of axial coincidence with piston 161. This action assures that the thread 152 of the plunger 151 remains parallel at all times to the thread 15 of the threaded cylinder 5. When the thread 152 of the plunger 151 is released from engagement with the thread 15 of the threaded cylinder 5, the direction of travel of the distal tip 155 of the plunger 151 relative to the piston 161 is dictated by the engagement of its angled retention barbs 154 with the receptacle slots 166 and the interface of its sliding guide plane 157 with the face of the angled ramp 165 upon which it bears. Preferably, both angled retention barbs 154 and their respective engaging receptacle slots 166 are arranged to lie parallel to the sliding guide plane 157 of the plunger 151.

The direction of travel of the lifter tip 43 of the thread control blade 3 is dictated by the angled fingers 18 of the thread control blade 3. Therefore, whenever the thread control blade 3 is actuated by pressing the control button 12, the lifter tip 43 moves distally as it moves transversely away from the rotational axis of the plunger 151. Consequently, this motion of the lifter tip 43 attempts to shove the plunger 151 axially away from the piston 161 at the same time it is being pushed transversely away from the adjacent semicircular wall 164 of the receptacle sleeve 162. Because the plunger 151 and piston 161 are retained to one another by the engagement of the angled retention barbs 154 grasping the receptacle slots 166, the longitudinal motion of the lifter tip 43 of the thread control blade 3 must be accommodated by sliding axially against the adjacent semicircular wall 164 of the receptacle sleeve 162. Friction generated by the lifter tip 43 of the thread control blade 3 sliding against the semicircular wall 164 increases the user input force required to depress the control button 12 during the initial stages of pressure release. However, due to the subtractive directionality imposed by the angled receptacle slots 166 and the guide plane 157 sliding against an abutting face of the angled ramps 165 as shown in FIG. 13, the overall longitudinal sliding distance of the lifter tip 43 against the semicircular wall 164 is less than its overall longitudinal extension. The reduced sliding distance of lifter tip 43 therefore decreases the duration of frictional resistance encountered by a user pressing the control button 12 when effecting pressure release of the device.

Each embodiment comprises a fluid displacement and pressurization device which provides both a substantial amount of thread engagement as well as provides for single hand control for all operational manipulations including maintaining a set fill volume, rapid filling and displacement, and pressurization and retention of evacuation positioning during balloon depressurization. Each embodiment allows for the use of one hand to not only transition the device from micro-movement control to macro-movement control, but also with regard to rotating, pushing or pulling the handle of the plunger.

While specific embodiments of the invention have been shown and described, it is envisioned that those skilled in the art may devise various modifications without departing from the spirit and scope of the present invention.

What is claimed is:

1. A fluid displacement and pressurization device comprising: a syringe body; a plunger which extends into the syringe body, said plunger comprising a thread and a longitudinal axis, said plunger having a groove which separates the thread; a piston on the plunger and in sealed contact with the syringe body; a control button pressable into the plunger; a threaded cylinder in the syringe body, said threaded cylinder comprising a thread; a pair of control blades configured to selectively engage and disengage the thread of the plunger with the thread of the threaded cylinder depending on whether the control button is pressed, wherein one of the control blades is positioned along the thread of the plunger and operates within the groove which separates the thread, wherein when the thread of the threaded cylinder is engaged with the thread of the plunger, the plunger is rotatable to provide micro-movement of the plunger relative to the syringe body, and wherein when the thread of the threaded cylinder is disengaged from the thread of the plunger, the plunger is pushable into the syringe body and pullable out of the syringe body to provide macro-movement of the plunger relative to the syringe body.

2. A fluid displacement and pressurization device as recited in claim 1, wherein the plunger comprises a shaft along the longitudinal axis, wherein the shaft is geometrically divisible into two zones by a longitudinal geometric plane disposed through the longitudinal axis, wherein a first zone of the two zones is provided with said thread of the plunger and a second zone of the two zones contains no thread.

3. A fluid displacement and pressurization device as recited in claim 1, wherein the pair of control blades comprises a thrust control blade which is configured to move inward toward the longitudinal axis of the plunger to effect disengagement of the thread of the threaded cylinder from the thread of the plunger.

4. A fluid displacement and pressurization device as recited in claim 1, wherein the control button engages the control blades and moves the control blades longitudinally proximal and distal.

5. A fluid displacement and pressurization device as recited in claim 1, further comprising a handle and spring which bears against the handle and drives the control button out from the handle.

6. A fluid displacement and pressurization device as recited in claim 1, wherein the plunger comprises the groove which separates the thread and comprises another groove, wherein another of the control blades is disposed in the other groove.

7. A fluid displacement and pressurization device as recited in claim 6, wherein the other groove is opposite the thread on the plunger.

8. A fluid displacement and pressurization device as recited in claim 1, wherein the device is configured to shift a rotational axis of the plunger away from a center axis of the threaded cylinder upon the control button being pressed.

9. A fluid displacement and pressurization device as recited in claim 1, wherein the piston and plunger are coupled together such that the plunger is shiftable relative to the piston causing the thread of the plunger to disengage from the thread of the threaded cylinder.

10. A fluid displacement and pressurization device as recited in claim 9, wherein shifting of the plunger relative to the piston is driven by at least one of the control blades.

11. A fluid displacement and pressurization device as recited in claim 10, wherein at least one of the control blades comprises a lifter tip which drives the shifting of the plunger.

12. A fluid displacement and pressurization device as recited in claim 1, further comprising a handle, wherein the control button floats in the handle and tracks the control blades when the control button is pressed into the handle.

13. A fluid displacement and pressurization device as recited in claim 1, wherein each of the control blades comprises a series of angled fingers, wherein the control blades are joined to one another by interlocking features which are provided at ends of the angled fingers.

14. A fluid displacement and pressurization device as recited in claim 1, wherein the plunger comprises a guide groove which provides a series of thrust blade control cams, wherein at least one of the control blades comprises a series of cam followers which ride up onto and bear against the control cams.

15. A fluid displacement and pressurization device as recited in claim 1, further comprising at least one locking key which anchors the threaded cylinder to the syringe body.

16. A fluid displacement and pressurization device as recited in claim 1, wherein the plunger comprises a distal end, wherein the piston comprises a receptacle sleeve having parallel flat sidewalls joined by semicircular walls which receive the distal end of the plunger.

17. A fluid displacement and pressurization device as recited in claim 16, wherein each of the parallel flat sidewalls of the receptacle sleeve is provided with angularly disposed receptacle slots, wherein a bottom of the receptacle sleeve is configured with a pair of planar faced angled ramps.

18. A fluid displacement and pressurization device as recited in claim 17, wherein the plunger comprises a distal tip, wherein the distal tip of the plunger comprises a pair of flat parallel sides, wherein both flat parallel sides comprise angled retention barbs which engage and retain into angled receptacle slots of the receptacle sleeve.

19. A fluid displacement and pressurization device as recited in claim 18, wherein the distal tip of the plunger comprises two angularly disposed planar surfaces comprising an abutment plane and a sliding guide plane, wherein both the abutment plane and the sliding guide plane align with and engage the angled ramps within the receptacle sleeve.

20. A fluid displacement and pressurization device as recited in claim 19, wherein the two angularly disposed planar surfaces are oriented perpendicular to the flat parallel sides of the distal tip of the plunger and are symmetrically arrayed about a rotational axis of the plunger.

21. A fluid displacement and pressurization device as recited in claim 1, wherein each of the control blades comprises a tab which engages a hook of the control button.

22. A fluid displacement and pressurization device as recited in claim 21, wherein when the control button is pushed into the handle, the control button translates relative to the control blade that is positioned along the thread of the plunger and which operates within the groove which separates the thread of the plunger.

23. A fluid displacement and pressurization device comprising: a syringe body; a plunger which extends into the syringe body, said plunger comprising a thread and a longitudinal axis; a piston on the plunger and in sealed contact with the syringe body; a control button pressable into the plunger; a threaded cylinder in the syringe body, said threaded cylinder comprising a thread;
   a pair of control blades configured to selectively engage and disengage the thread of the plunger with the thread of the threaded cylinder depending on whether the control button is pressed, wherein when the thread of the threaded cylinder is engaged with the thread of the plunger, the plunger is rotatable to provide micro-movement of the plunger relative to the syringe body, and wherein when the thread of the threaded cylinder is disengaged from the thread of the plunger, the plunger is pushable into the syringe body and pullable out of the syringe body to provide macro-movement of the plunger relative to the syringe body, wherein each of the control blades comprises a series of angled fingers, wherein the control blades are joined to one another by interlocking features which are provided at ends of the angled fingers.

24. A fluid displacement and pressurization device as recited in claim 23, wherein the plunger comprises a guide groove which provides a series of thrust blade control cams, wherein at least one of the control blades comprises a series of cam followers which ride up onto and bear against the control cams.

25. A fluid displacement and pressurization device comprising: a syringe body; a plunger which extends into the syringe body, said plunger comprising a thread and a longitudinal axis; a piston on the plunger and in sealed contact with the syringe body; a control button pressable into the plunger; a threaded cylinder in the syringe body, said threaded cylinder comprising a thread; a pair of control blades configured to selectively engage and disengage the thread of the plunger with the thread of the threaded cylinder depending on whether the control button is pressed, wherein when the thread of the threaded cylinder is engaged with the thread of the plunger, the plunger is rotatable to provide micro-movement of the plunger relative to the syringe body, and wherein when the thread of the threaded cylinder is disengaged from the thread of the plunger, the plunger is pushable into the syringe body and pullable out of the syringe body to provide macro-movement of the plunger relative to the syringe body, wherein the plunger comprises a guide groove which provides a series of thrust blade control cams, wherein at least one of the control blades comprises a series of cam followers which ride up onto and bear against the control cams.

* * * * *